(12) United States Patent
Khalifa et al.

(10) Patent No.: US 10,100,054 B1
(45) Date of Patent: Oct. 16, 2018

(54) PYRIDO[2,3-D]PYRIMIDINES AS ANTICANCER AGENTS

(71) Applicant: KING SAUD UNIVERSITY, Riyadh (SA)

(72) Inventors: Nagy Mahmoud Hassan Khalifa, Riyadh (SA); Mohamed A. Al-Omar, Riyadh (SA); Hamad M. Alkahtani, Riyadh (SA); Ahmed H. Bakheit, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/944,734

(22) Filed: Apr. 3, 2018

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 7,067,658 B2 | 6/2006 | Sielecki-Dzurdz et al. |
| 7,825,242 B2 | 11/2010 | Feng et al. |
| 8,133,898 B2 | 3/2012 | Gwaltney et al. |
| 8,354,526 B2 | 1/2013 | Ding et al. |
| 8,563,579 B2 | 10/2013 | Kanner |
| 9,624,218 B2 | 4/2017 | Chedid et al. |

OTHER PUBLICATIONS

Youssef et al. Phosphorous, Sulfur, Silicon and the Related Elements, 44 (3-4), 197-201 (1989) (Year: 1989).*
Shujiang Tu et al., "New potential inhibitors of cyclin-dependent kinase 4:Design and synthesis of pyrido[2,3-d] pyrimidine derivatives under microwave irradiation", Bioorganic & Medicinal Chemistry Letters (2006) vol. 16, pp. 3578-3581.
El-Nassan, "Synthesis and antitumor activity of novel pyrido[2,3-d][1,2,4]triazolo[4,3-a]pyrimidin-5-one derivatives", European Journal of Medicinal Chemistry (2011), 46, 2031-2036.
C. Kurumurthy et al., "Synthesis of novel alkyltriazole tagged pyrido[2,3-d]pyrimidine derivatives and their anticancer activity", European Journal of Medicinal Chemistry (2011) 46, 3462-3468.
Ibrahim et al., "Design, synthesis and biological study of novel pyrido[2,3-d]pyrimidine as anti-proliferative CDK2 inhibitors", (2011) 46, 5825-5832.
Lam et al., "Structure-based design of pyridopyrimidines as dipeptidyl peptidase IV inhibitors", Bioorganic & Medicinal Chemistry Letters (2012), 22(21) 6628-6631.
Palop et al., "Novel quinazoline and pyrido[2,3-d]pyrimidine derivatives and their hydroselenite salts as antitumoral agents", ARKIVOC: Archive for Organic Chemistry (2014) vol. 8, 187-206.

Fares et al., "Synthesis and antitumor activity of pyrido[2,3-d]pyrimidine and pyrido[2,3-d][1,2,4]triazolo[4,3-a] pyrimidine derivatives that induce apoptosis through G1 cell-cycle arrest", European Journal of Medicinal Chemistry (2014), 83 155-166.
Edupuganti et al., "Synthesis and biological evaluation of pyrido[2,3-d]pyrimidine-2,4-dione derivatives as eEF-2K inhibitors", Bioorganic & Medicinal Chemistry (2014), 22, 4910-4916.
Ziarani et al.; "One-pot synthesis of pyrido[2,3-d]pyrimidine derivatives using sulfonic acid functionalized SBA-15 and the study on their antimicrobial activities", Journal of Saudi Chemical Society (2014) 19, 676-681.
Nkizinkiko et al., "Discovery of potent and selective nonplanar tankyrase inhibiting nicotinamide mimics", Bioorganic & Medicinal Chemistry (2015) 23(15) 4139-4149.
Kumar et al., "Synthesis of novel triazole/isoxazole functionalized 7-(trifluoromethyl)pyrido[2,3-d]pyrimidine derivatives as promising anticancer and antibacterial agents", Bioorganic & Medicinal Chemistry Letters (2016), 26, 2927-2930.
Hou et al., "Design, synthesis, anti-tumor activity, and molecular modeling of quinazoline and pyrido[2,3-d]pyrimidine derivatives targeting epidermal growth factor receptor", European Journal of Medicinal Chemistry (2016), 118, 276-289.
El-Naggar et al., "Eco-friendly synthesis of Pyrido[2,3-d]pyrimidine Analogs and Their Anti-cancer and Tyrosine Kinase Inhibition Activities", Anticancer Agents Med Chem (2017), 17(12) 1644-1651 (Abstract only).
Elzahabi et al., "Anticancer evaluation and molecular modeling of multi-targeted kinase inhibitors based pyrido[2,3-d] pyrido[2,3-d]pyrimidinescaffold", Journal of Enzyme Inhibition and Medicinal Chemistry (2018), 33(1), 37 pages.

* cited by examiner

*Primary Examiner* — Dennis Heyer
(74) *Attorney, Agent, or Firm* — Richard C. Litman

(57) ABSTRACT

The pyrido[2,3-d]pyrimidine derivatives as anticancer agents include 5-(substituted-phenyl)-2-(3-methyl-5-oxo-2H-pyrazol-1(5H)-yl)-7-(pyridin-3-yl)pyrido[2,3-d]pyrimidin-4(3H)-one derivatives having the formula:

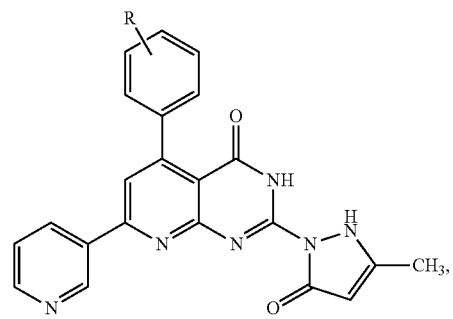

where R is hydrogen; 2-halo, 3-halo, or 4-halo (Cl, Br, or F); 2-methoxy, 3-methoxy, or 4-methoxy ($OCH_3$); 2-nitro, 3-nitro, or 4-nitro ($NO_2$); 4-isopropyl, 4-methyl, or 4-cyano (CN); 2-hydroxy or 3-hydroxy (OH), 3-chloro and 5-chloro; 2-methoxy and 5-methoxy, 3-methoxy and 5-methoxy, or 3-methoxy and 4-methoxy; 3,4,5-trimethoxy; or 2-hydroxy and 4-hydroxy; or a pharmaceutically acceptable salt thereof. The derivatives may be useful in treating various cancers, including hepatic, colon, prostate, breast, and lung cancer.

6 Claims, 2 Drawing Sheets

PYRIDO[2,3-D]PYRIMIDINES AS ANTICANCER AGENTS

BACKGROUND

1. Field

The disclosure of the present patent application relates to compounds useful as anticancer agents, and particularly to pyrido[2,3-d]pyrimidine derivatives as anticancer agents that may provide multi-targeted kinase inhibitors for various forms of cancer.

2. Description of the Related Art

Cancer is one of the leading causes of death in the world, primarily characterized by a loss of control of cell growth leading to death. Chemotherapy remains one of the primary modalities for the treatment of cancer. However, the use of available chemotherapeutics is limited, mainly due to drug resistance and toxicity. Resistance to chemotherapy may develop by many pathways, such as poor uptake of the drug, triggering of alternative metabolic paths, increased production of target proteins, mutations that block the drug from binding to target proteins, or efflux systems that expel drugs from cells. Combinations of chemotherapeutic agents are often pursued, as targeting different proteins increases chemotherapeutic efficiency, antagonizes resistance development, and decreases toxicity effects.

Traditional anticancer drugs work by disrupting the function of DNA, typically by either affecting DNA directly or by disrupting enzymes controlling DNA synthesis. Such drugs are nonselective and cytotoxic to both cancer cells and normal cells. Advances in molecular biology and genetics have led to improved identification of molecular targets that are unique to, or over expressed in, cancer cells. The design of agents affecting these targets is a promising strategy to develop more selective anticancer drugs with less toxic side effects.

Thus, pyrido[2,3-d]pyrimidine derivatives as anticancer agents solving the aforementioned problems are desired.

SUMMARY

The pyrido[2,3-d]pyrimidine derivatives as anticancer agents include 5-(substituted-phenyl)-2-(3-methyl-5-oxo-2H-pyrazol-1(5H)-yl)-7-(pyridin-3-yl)pyrido[2,3-d]pyrimidin-4(3H)-one derivatives having the formula:

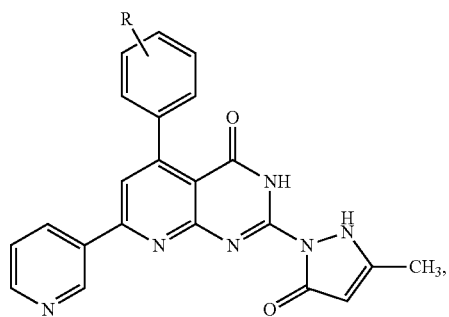

where R is hydrogen; 2-halo, 3-halo, or 4-halo (Cl, Br, or F); 2-methoxy, 3-methoxy, or 4-methoxy (OCH$_3$); 2-nitro, 3-nitro, or 4-nitro (NO$_2$); 4-isopropyl, 4-methyl, or 4-cyano (CN); 2-hydroxy or 3-hydroxy (OH), 3-chloro and 5-chloro; 2-methoxy and 5-methoxy, 3-methoxy and 5-methoxy, or 3-methoxy and 4-methoxy; 3,4,5-trimethoxy; or 2-hydroxy and 4-hydroxy; or a pharmaceutically acceptable salt thereof.

Preferred embodiments include a compound of the above formula wherein R is a methoxy group, and more particularly a compound having the following structure:

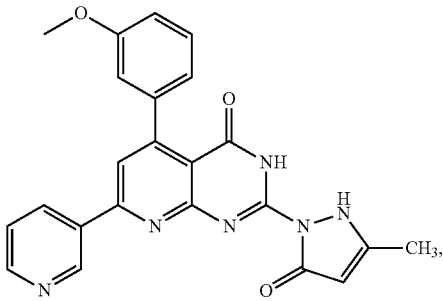

or a pharmaceutically acceptable salt thereof.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The pyrido[2,3-d]pyrimidine derivatives as anticancer agents include 5-(substituted-phenyl)-2-(3-methyl-5-oxo-2H-pyrazol-1(5H)-yl)-7-(pyridin-3-yl)pyrido[2,3-d]pyrimidin-4(3H)-one derivatives having the formula:

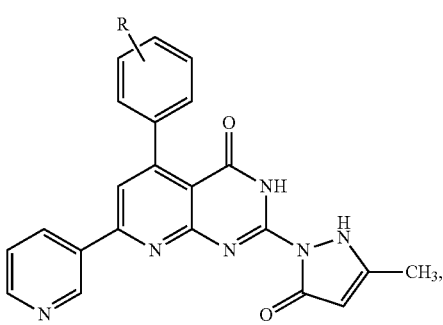

where R is hydrogen; 2-halo, 3-halo, or 4-halo (Cl, Br, or F); 2-methoxy, 3-methoxy, or 4-methoxy (OCH$_3$); 2-nitro, 3-nitro, or 4-nitro (NO$_2$); 4-isopropyl, 4-methyl, or 4-cyano (CN); 2-hydroxy or 3-hydroxy (OH), 3-chloro and 5-chloro; 2-methoxy and 5-methoxy, 3-methoxy and 5-methoxy, or 3-methoxy and 4-methoxy; 3,4,5-trimethoxy; or 2-hydroxy and 4-hydroxy; or a pharmaceutically acceptable salt thereof. It will be understood by those of ordinary skill in the art that the above general formula uses R to include both mono-substituted substituents and multiple substitutions (such as di-substituted and tri-substituted) using numbering based on the available carbons of the phenyl substituent, rather than using the conventional R1, R2, R3, etc. with lists of independent substituents, for the sake of compactness in presentation.

Preferred embodiments include a compound of the above formula wherein R is 2-methoxy, 3-methoxy, or 4-methoxy, and more particularly a compound having the following structure:

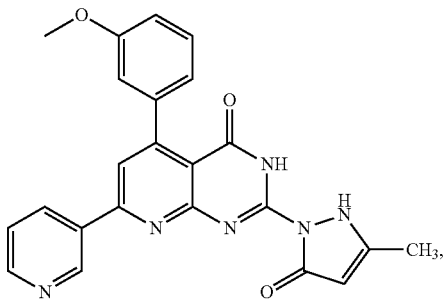 [SMILES: COc1cccc(-c2cc(-c3cccnc3)nc3nc(-n4[nH]c(C)cc4=O)[nH]c(=O)c23)c1]

or a pharmaceutically acceptable salt thereof.

Still other embodiments include a method of treating a cancer patient, comprising the step of administering a pharmaceutical composition including an effective amount of any of compound according to the present application to a patient in need thereof. The cancer patient being treated according to the above disclosed methods may preferably have been diagnosed with at least one of hepatic cancer, prostate cancer or colon cancer.

The pyrido[2,3-d]pyrimidine derivatives as anticancer agents provide effective anticancer activity, as will be demonstrated in the Examples provided below. The new pyrido [2,3-d]pyrimidine derivatives demonstrate higher potency in providing anticancer relief ($GI_{50}$: 0.3 µM) compared to the reference standard doxorubicin ($IC_{50}$: 0.6 µM). These results demonstrate that the pyrido[2,3-d]pyrimidine derivative exerts acute anticancer action against hepatic cancer (HepG-2), prostate cancer (PC-3) and colon cancer (HCT-116) cell lines, suggesting that it may represent an alternative in the development of new therapeutic strategies.

Figure 3:
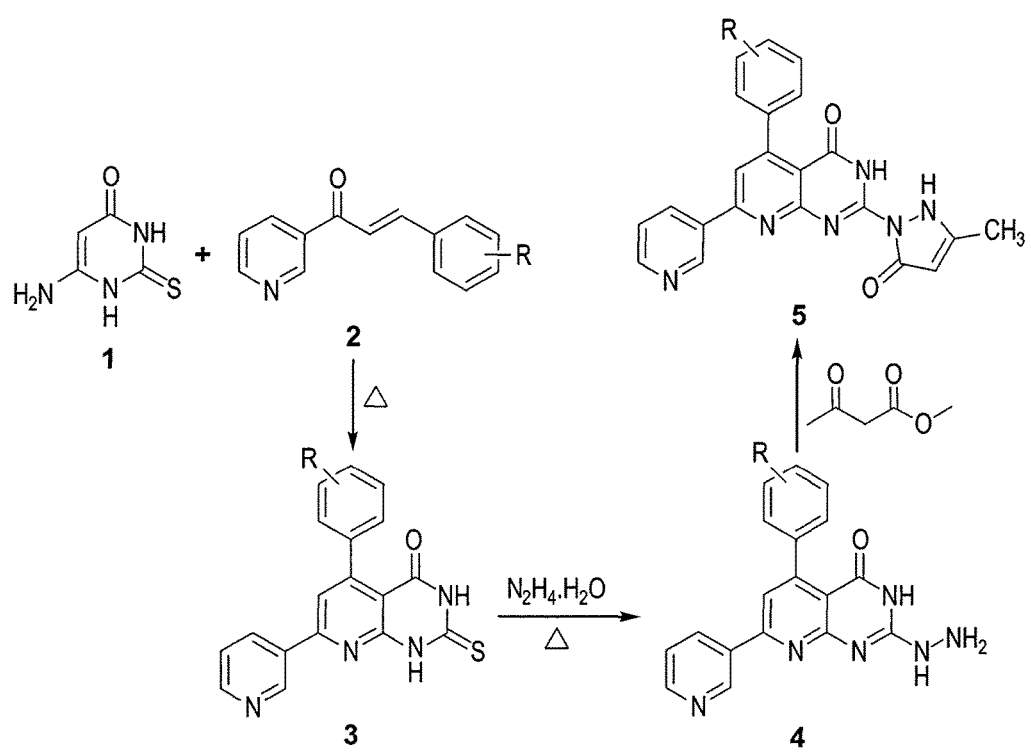
FIG. 3 is a reaction scheme for synthesizing the pyrido[2,3-d]pyrimidine derivatives of the present application.

Referring to FIG. 3, the pyrido[2,3-d]pyrimidine derivatives 5 were synthesized through reaction of a starting precursor, 2-mercapto-4-hydroxy-6-aminopyrimidine 1, with the α,β unsaturated ketone 2 in suitable solvent to afford the corresponding thioxo derivative 2,3-dihydro-5-(substituted phenyl)-7-(pyridin-3-yl)-2-thioxo-pyrido[2,3-d] pyrimidin-4(1H)-one 3. Nucleophilic attack of hydrazine hydrate on the thioxo derivative 3 afforded the corresponding hydrazine derivative 2-hydrazinyl-5-(substituted phenyl)-7-(pyridin-3-yl)pyrido[2,3-d]pyrimidin-4(3H)-one 4. The hydrazine derivative 4 was reacted with ethylacetoacetate as active methylene compound in glacial acetic acid to give the target product 5-(substituted phenyl)-2-(3-methyl-5-oxo-2H-pyrazol-1(5H)-yl)-7-(pyridin-3-yl) pyrido[2,3-d] pyrimidin-4(3H)-one 5.

Figure 1:
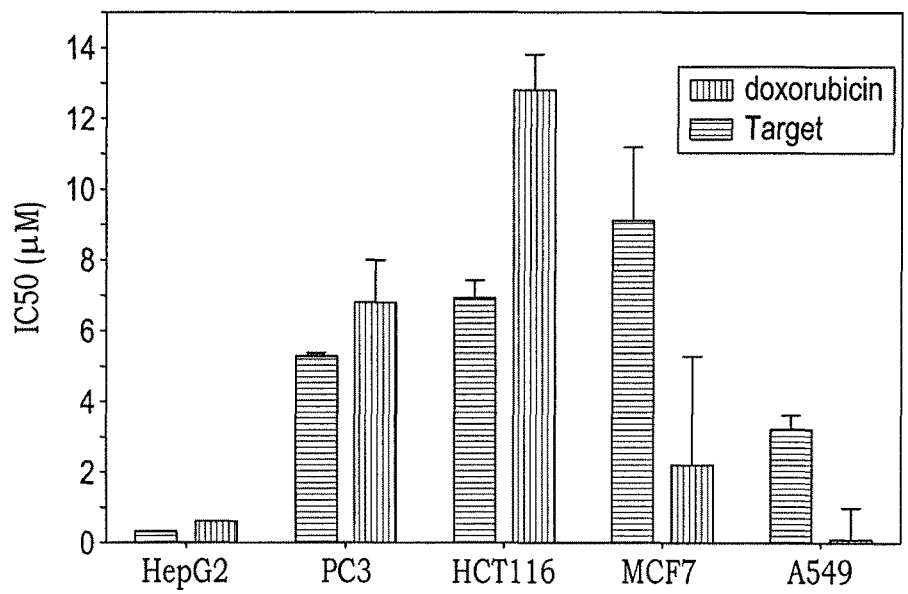
FIG. 1 is a plot showing IC$_{50}$ of the preferred pyrido[2,3-d]pyrimidine derivative against HepG2, PC-3, HCT116, MCF-7 and A549 cell lines resulting from tests of Example 2.
Figure 2:
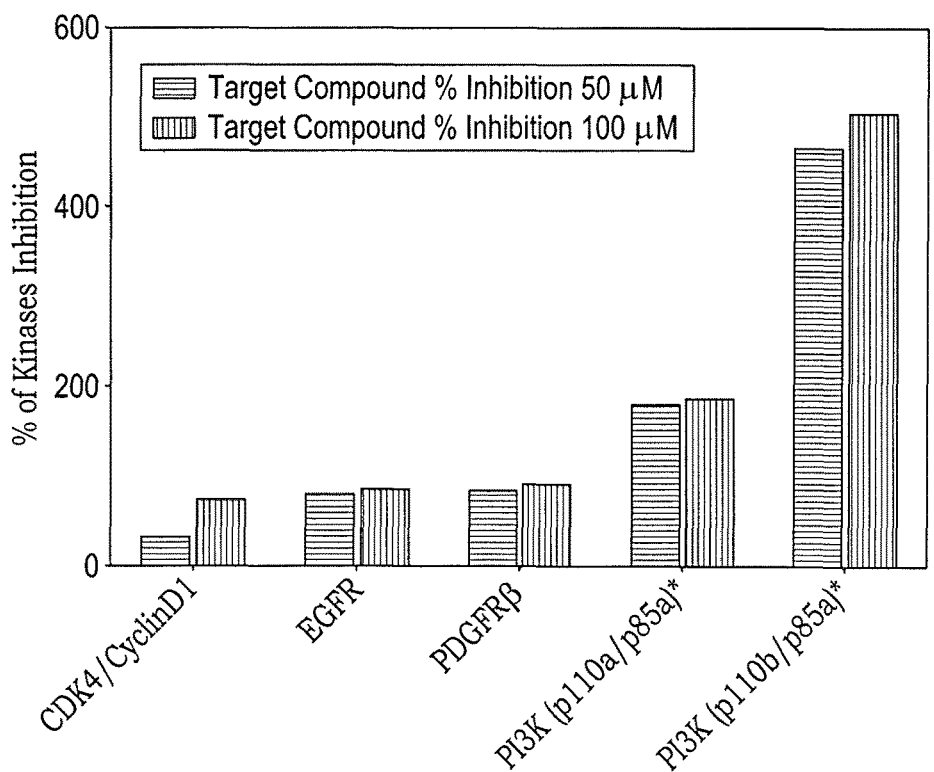
FIG. 2 is a plot summarizing the kinase inhibition activity of the preferred pyrido[2,3-d]pyrimidine derivative against CDK4, EGFR and PDGFRβ, at concentrations of 50 μM and 100 μM.

Anticancer evaluation of the pyrido[2,3-d]pyrimidine derivatives was performed against five cancer cell lines, namely, hepatic cancer (HePG-2), prostate cancer (PC-3), colon cancer (HCT-116), breast cancer (MCF-7), and lung cancer (A-549) cell lines. The in vitro screening of the pyrido[2,3-d]pyrimidine derivative at 100 mM exhibited remarkable anticancer activity, which was twice the activity compared with that of doxorubicin ($IC_{50}$ of 0.3 µM each and 0.6 µM, respectively) against the tested cell line anti-hepatic cancer activity (anti HepG2). See, for example, Tables 1-3 and FIGS. 1-2

TABLE 1

Percentage of growth inhibition at (100 µM) dose

| | Growth inhibition (%) | | | | |
|---|---|---|---|---|---|
| Compd. No | HepG2 | PC3 | HCT116 | MCF7 | A549 |
| Target | 100 | 100 | 99 | 87 | 99 |
| doxorubicin | 100 | 100 | 100 | 91 | 100 |

TABLE 2

$IC_{50}$ Values

| | $IC_{50}$ (µM) | | | | |
|---|---|---|---|---|---|
| Compd. No. | HepG2 | PC3 | HCT116 | MCF7 | A549 |
| Target | 0.3 ± 0.02 | 5.3 ± 0.09 | 6.9 ± 0.5 | 9.1 ± 2.1 | 3.21 ± 0.4 |
| doxorubicin | 0.6 ± 0.05 | 6.8 ± 1.2 | 12.8 ± 1 | 2.2 ± 3.1 | 0.087 ± 0.9 |

TABLE 3

Percentage of kinase inhibition at 50 µM and 100 µM dosage

| | Target compound % Inhibition | |
|---|---|---|
| Kinase | 50 µM | 100 µM |
| CDK4/CyclinD1 | −31 | −73 |
| EGFR | −79 | −85 |
| PDGFRβ | −83 | −90 |
| PI3K (p110a/p85a) * | 178 | 185 |
| PI3K (p110b/p85a) * | 465 | 503 |

Negative (−) values: Inhibition of target activity.
Positive (+) values: activation of target activity.

Computational docking studies of the pyrido[2,3-d]pyrimidine derivatives 5 with Epidermal Growth Factor Receptor (EGFR) were performed and the configuration of ligand-receptor was selected having the lowest energy interaction between ligand with receptor. In the selected configuration, two hydrogen bonds formed between compound 5 with a side chain of the hydrophobic residue of LEU 768 and MET 769 of the EGFR. The bond lengths are shown in Table 4. The docking experiment suggests that the pyrido [2,3-d]pyrimidine derivatives have high affinity towards EGFR with a docking score of −7.795. This affinity is attributed to strong hydrogen bonds between C═O of the pyrazolone and Leu768 (3.35 Å) and Met 769 (2.93 Å). In addition, pyridopyrimidine and methoxyphenyl are involved in relatively weak pi-hydrogen interactions with Val702, respectively. Table 4, below, shows the docking results of the pyrido[2,3-d]pyrimidine derivatives, interacting residues, distance between the protein and ligand (Å), hydrogen bond acceptor, and pi-H.

Docking studies and all modeling calculations were performed using program "Molecular Operating Environment" software package (MOE® 2015 version), which used for per-adjustment of receptor through removed water molecules and added hydrogen atoms. Also, MOE 2015 was used to graph the structure of the ligands' 3D, and to minimize the energy of structure and geometries of ligands, and then it was saved in data list. The pockets for each receptor were used to docking ligands data list after set London dG for scoring function and GBVI/WSA dG for rescoring function. The scoring and RMSD (root mean square deviation) values for best conformation of each ligand with different receptors were listed on table 4 based 2D and 3D figures of each selected conformation were tabulated. All the interaction energies and different calculations were automatically calculated.

TABLE 4

Docking compound 5 into EGFR in comparison to the co-crystallized ligand (erlotinib)

| receptor | Amino Acid Residues | Interaction Type | Distance (Å) | Total Binding Energy (kcal · mol$^{-1}$) | RMSD |
|---|---|---|---|---|---|
| EGFR (4HJO) | LEU 768 | H-acceptor | 3.35 | | |
| | MET 769 | H-acceptor | 2.93 | | |
| | VAL 702 | pi-H | 3.92 | −7.795 | 1.412 |
| | VAL 702 | pi-H | 4.05 | | |
| | ASP 831 | pi-H | 4.30 | | |

The pyrido[2,3-d]pyrimidine derivatives as anticancer agents were synthesized according to the reaction scheme shown in FIG. 3. In FIG. 3, R is hydrogen; 2-halo, 3-halo, or 4-halo (Cl, Br, or F); 2-methoxy, 3-methoxy, or 4-methoxy (OCH$_3$); 2-nitro, 3-nitro, or 4-nitro (NO$_2$); 4-isopropyl, 4-methyl, or 4-cyano (CN); 2-hydroxy or 3-hydroxy (OH), 3-chloro and 5-chloro; 2-methoxy and 5-methoxy, 3-methoxy and 5-methoxy, or 3-methoxy and 4-methoxy; 3,4,5-trimethoxy; or 2-hydroxy and 4-hydroxy. The scheme will be better understood with reference to the following examples.

Example 1

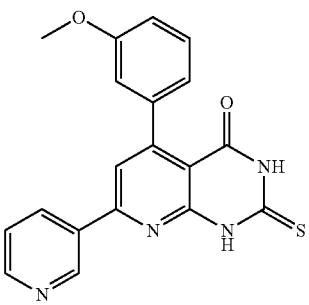

Synthesis of compound 3
2,3-Dihydro-5-(substitutedphenyl)-7-(pyridin-3-yl)-2-thioxo-pyrido[2,3-d]pyrimidin-4- (1H)-one A mixture of 6-amino-2,3-dihydro-2-thioxopyrimidin-4 (1H)-one (0.01 mol) and α, β-unsaturated ketones (0.01 mol) in suitable organic solvent (20 mL) was heated under reflux for 10-12 h and the progress of the reaction was monitored by TLC. The solid mass (compound 3 where R is 3-methoxy; see FIG. 3) obtained on cooling after completion of the reaction was filtered, dried and crystallized from proper solvent. Yield: 67%; mp: >300° C.; IR (KBr, cm$^{-1}$) v: 3427, 3385 (2NH), 1663 (C=O), 1328 (C=S); $^1$H NMR (DMSO-d$_6$): δ, 13.03, 12.34 (2s, 2H, D$_2$O exchangeable), 9.23 (s, 1H), 8.56-7.25 (m, 9H), 3.81 (s, 3H); $^{13}$C NMR (DMSO-d$_6$): δ 175.01, 159.97, 153.72, 153.02, 151.14, 149.65, 147.82, 137.66, 135.01, 134.59, 129.45, 127.19, 123.87, 113.21, 108.94, 59.47; MS: [m/z, 362 (M$^+$)]; Anal. Calcd for: C$_{19}$H$_{14}$N$_4$O$_2$S (362.41): C, 62.97; H, 3.89; N, 15.46% Found: C; 62.82, H, 3.75; N, 15.29%.

Example 2

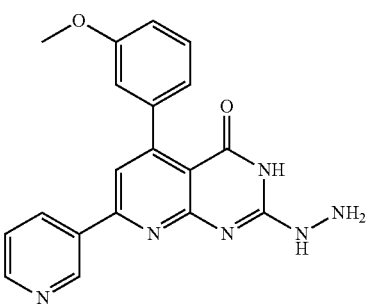

Synthesis of compound 4
2-Hydrazinyl-5-(substitutedphenyl)-7-(pyridin-3-yl) pyrido[2,3-d]pyrimidin-4(3H)-one A mixture of 2-thioxopyrido[2,3-d]pyrimidine derivative (0.003 mol) and hydrazine hydrate 99% (0.005 mol) was heated under reflux in suitable organic solvent (30 mL) for 12 h. The solid (compound 4 where R is 3-methoxy; see FIG. 3) formed on cooling was filtered, dried and crystallized from proper solvent. Yield: 72%; mp: 296-298° C.; IR (KBr, cm$^{-1}$) v: 3365, 3290 (NH$_2$, NH), 1680 (C=O); $^1$H NMR (DMSO-d$_6$): δ, 12.45, 9.26 (2s, 2H, D$_2$O exchangeable), 9.21 (s, 1H), 8.62-7.23 (m, 9H), 5.20 (s, 2H, D$_2$O exchangeable), 3.79 (s, 3H); $^{13}$C NMR (DMSO-d$_6$): δ 162.41, 159.97, 153.12, 152.47, 151.93, 149.96, 147.83, 137.21, 135.01, 134.57, 130.01, 129.17, 126.38, 123.90, 121.02, 118.74, 56.38; MS: [m/z, 360 (M$^+$)]; Anal. Calcd for: C$_{19}$H$_{16}$N$_6$O$_2$ (360.37): C, 63.32; H, 4.48; N, 23.32% Found: C; 63.18, H, 4.32; N, 23.14%.

Example 3

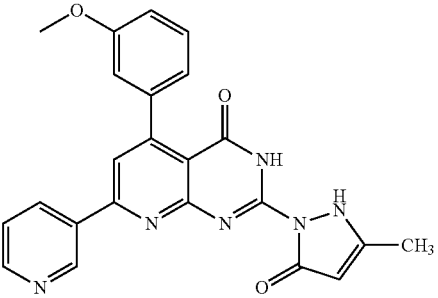

Synthesis of compound 5
5-(3-Substitutedphenyl)-2-(3-methyl-5-oxo-2H-pyrazol-1(5H)-yl)-7-(pyridin-3-yl) pyrido-[2,3-d]pyrimidin-4-(3H)-one A mixture of 2-Hydrazinylpyrido[2,3-d]pyrimidinone 4 (0.01 mol) and ethyl acetoacetate (0.01 mol) in suitable organic solvent (15 mL) was refluxed for 7 h. After completion of the reaction, the reaction mixture was poured into ice-water and the precipitate (compound 5 where R is 3-methoxy; see FIG. 3) formed was filtered, dried and crystallized from proper solvent. Yield: 49%; mp: >300° C.; IR (KBr, cm$^{-1}$) v: 3367, 3210 (2NH), 1723, 1665 (2C=O); $^1$H NMR (DMSO-d$_6$): δ 12.76, 11.24 (2s, 2H, D$_2$O exchangeable), 8.67-7.11 (m, 9H), 3.79 (s, 3H), 1.87 (s, 3H); $^{13}$C NMR (DMSO-d$_6$): δ 165.14, 164.32, 161.24, 161.10, 153.09, 152.64, 152.18, 151.87, 150.48, 147.99, 139.12, 135.01, 134.52, 129.85, 123.68, 121.06, 119.82, 119.25, 115.76, 112.36, 105.47, 56.28, 24.31; MS: [m/z, 426 (M$^+$)]; Anal. Calcd for: C$_{23}$H$_{18}$N$_6$O$_3$ (426.43): C, 64.78; H, 4.25; N, 19.71% Found: C, 64.61; H, 4.09; N, 19.59%.

Example 4

Methodology of In Vitro Anticancer Screening

Anticancer activity screening was adopted against five cancer cell lines, viz., HepG2, PC-3, HCT116, MCF-7, A549, and doxorubicin was used as a reference standard at 100 micromole.

Cell viability was assessed by the mitochondrial dependent reduction of yellow MTT (3-(4,5-dimethylthiazol-2-yl)-2,5-diphenyl tetrazolium bromide) to purple formazan. All the following procedures were done in a sterile area using a laminar air flow cabinet of class II biosafety (Baker, SG403INT, Sanford, Me., USA). Cells were suspended in DMEM medium for PC-3, and RPMI1640 in case of A-549, MCF-7, HCT-116 and HePG-2. The media are supplemented with 1% antibiotic antimycotic mixture (10,000 U ml$^{-1}$ Potassium Penicillin, 10,000 μg ml$^{-1}$ Streptomycin Sulfate and 25 μg ml$^{-1}$ Amphotericin B), 1% L-glutamine and 10% fetal bovine serum (complete growth medium) and kept at 4° C. under 5% CO$_2$. Cells were batch cultured for 10 days, then seeded at a concentration of 10×103 cells/well in fresh complete growth medium in 96-well Microtiter plastic plates at 37° C. for 24 h under 5% CO$_2$ and a humid atmosphere using a water jacketed carbon dioxide incubator (Sheldon, TC2323, Cornelius, Oreg., USA). Media was aspirated, fresh medium (without serum) was added, and cells were incubated either alone (negative control) or with serial dilutions of each sample. After 48 h of incubation, the medium was aspirated, 40 μl MTT salt (2.5 μg ml$^{-1}$) was added to each well and incubated for a further four hours at 37° C. under 5% CO$_2$. To stop the reaction and dissolving the formed crystals, 200 μl of 10% sodium dodecyl sulfate (SDS) in deionized water was added to each well and incubated overnight at 37° C. The absorbance was then measured using a microplate multi-well reader ELISA reader (Bio-Rad Laboratories Inc., model 3350, Hercules, Calif., USA) at 595 nm and a reference wavelength of 620 nm. A statistical significance was tested between samples and negative control (cells with vehicle) using independent t-test by SPSS 11 program. DMSO is the vehicle used for dissolution of plant extracts, and its final concentration in the cells was less than 0.2%. The percentage of change in viability was calculated according to the formula: (average absorbance of extract/average absorbance of negative control)−1)×100. A probit analysis was carried for IC$_{50}$ determination using SPSS 11 program.

Example 5

Methodology of Kinase Screening

The in vitro enzyme inhibition determination for the pyrido[2,3-d]pyrimidine derivatives was performed against a range of five protein kinases [PDGFR beta, EGFR, CDK4/Cyclin D1, PI3K (p100b/p85a), and PI3K (p100a/p85a)], including two concentrations (50 & 100 μM) in single measurements using the radiometric or ADP-Glo assay method. The intra-assay variability was determined to be less than 10%. Inhibition of target activity by the compound gives negative (−) values, while activation of target activity gives positive (+) value.

The pyrido[2,3-d]pyrimidine derivative 5 was supplied by Kinexus as a powder, and a stock solution was made in DMSO. The stock solution was then diluted to form an assay stock solution, and this was used to profile against the protein kinases and lipid protein kinases [PDGFR beta, EGFR, CDK4/Cyclin D1, PI3K (p100b/p85a), and PI3K (p100a/p85a)]. The assay condition for the protein kinase targets was optimized to yield acceptable enzymatic activity. In addition, the assays were optimized to give high signal-to-noise ratio.

For Protein Kinase (PK) Assays, a radioisotope assay format was used for profiling evaluation of PK targets and all assays were carried out in a designated radioactive working area. PK assays (in singlicate) were performed at ambient temperature for 30 min in a final volume of 25 μl according to the following assay reaction recipe: Component 1:5 μl of diluted active PK target (~10-50 nM final concentration); Component 2:5 μl of stock solution of substrate (1-5 μg of peptide substrate); Component 3:5 μl of kinase assay buffer; Component 4:5 μl of compound (50 μM) or 10% DMSO; and Component 5:5 μl of $^{33}$P-ATP (250 μM stock solution, 0.8 μCi).

The assay was initiated by the addition of $^{33}$P-ATP, and the reaction mixture incubated at ambient temperature for 30 minutes. After the incubation period, the assay was terminated by spotting 10 μl of the reaction mixture onto Multiscreen phosphocellulose P81 plate. The Multiscreen phosphocellulose P81 plate was washed 3 times for approximately 15 min each in a 1% phosphoric acid solution. The radioactivity on the P81 plate was counted in the presence of scintillation fluid in a Trilux scintillation counter. Blank control was set up that included all the assay components except the addition of the appropriate substrate (replaced with equal volume of assay dilution buffer). The corrected activity for PK target was determined by removing the blank control value.

It is to be understood that the anticancer agents of multi-targeted kinase inhibitors based on pyrido[2,3-d]pyrimidines is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pyrido[2,3-d]pyrimidine derivative as anticancer agent, comprising a compound having the formula:

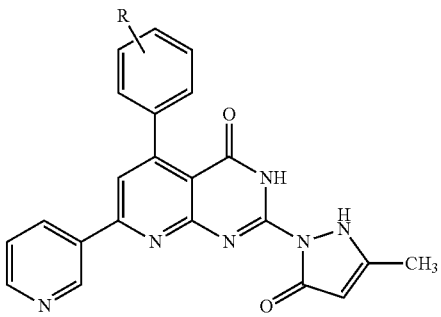

where R is hydrogen; 2-halo, 3-halo, or 4-halo (where halo is Cl, Br, or F); 2-methoxy, 3-methoxy, or 4-methoxy ($OCH_3$); 2-nitro, 3-nitro, or 4-nitro ($NO_2$); 4-isopropyl, 4-methyl, or 4-cyano (CN); 2-hydroxy or 3-hydroxy (OH), 3-chloro and 5-chloro; 2-methoxy and 5-methoxy, 3-methoxy and 5-methoxy, or 3-methoxy and 4-methoxy; 3,4,5-trimethoxy; or 2-hydroxy and 4-hydroxy;

or a pharmaceutically acceptable salt thereof.

2. The pyrido[2,3-d]pyrimidine derivative of claim 1, wherein R is selected from the group consisting of 2-methoxy, 3-methoxy and 4-methoxy.

3. A pharmaceutical composition, comprising:
the compound according to claim 2; and
a pharmaceutically acceptable carrier.

4. A pharmaceutical composition, comprising:
the compound according to claim 1; and
a pharmaceutically acceptable carrier.

5. A method of making a pyrido[2,3-d]pyrimidine derivative according to claim 1, comprising the steps of:
heating a first mixture of 6-amino-2,3-dihydro-2-thioxopyrimidin-4(1H)-one and an α, β unsaturated ketone having the formula:

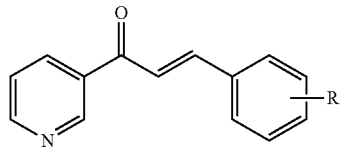

in an organic solvent under reflux;
cooling the heated first mixture to precipitate a first intermediate product;
heating a second mixture of the first intermediate product and hydrazine hydrate in an organic solvent under reflux;
cooling the heated second mixture to precipitate a second intermediate product;
heating a third mixture of the second intermediate product and ethyl acetoacetate in an organic solvent under reflux;
pouring the heated third mixture into ice water to precipitate the pyrido[2,3-d]pyrimidine derivative.

6. A method for achieving an effect in a patient, comprising administering an effective amount of a pyrido[2,3-d]pyrimidine derivative according to claim 1 to the patient, wherein the effect is inhibiting growth of a hepatic cancer tumor, a prostate cancer tumor, a colon cancer tumor, a breast cancer tumor, or a lung cancer tumor; or the effect is inhibiting a kinase selected from the group consisting of PDGFR, EGFR, CDK4/Cyclin D1, PI3K (p100b/p85a), and PI3K (p100a/p85a).

* * * * *